// 
US008784714B2

(12) United States Patent
Horrisberger et al.

(10) Patent No.: US 8,784,714 B2
(45) Date of Patent: Jul. 22, 2014

(54) STEROID ELUTING COLLAR UNDERMOLD

(71) Applicant: Cardiac Pacemakers, Inc., St. Paul, MN (US)

(72) Inventors: Benn Horrisberger, Blaine, MN (US); Joel T. Eggert, Plymouth, MN (US); Kimberly A. Morris, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 13/760,326

(22) Filed: Feb. 6, 2013

(65) Prior Publication Data

US 2013/0261714 A1    Oct. 3, 2013

Related U.S. Application Data

(60) Provisional application No. 61/617,966, filed on Mar. 30, 2012.

(51) Int. Cl.
| | |
|---|---|
| *B29C 45/14* | (2006.01) |
| *B29C 69/02* | (2006.01) |
| *A61N 1/05* | (2006.01) |
| *B29C 65/00* | (2006.01) |
| *B29K 71/00* | (2006.01) |
| *B29L 23/00* | (2006.01) |
| *B29C 65/02* | (2006.01) |
| *B29K 83/00* | (2006.01) |
| *B29L 31/00* | (2006.01) |

(52) U.S. Cl.
CPC ... *B29C 45/14549* (2013.01); *B29C 2045/1477* (2013.01); *B29C 66/91945* (2013.01); *B29C 66/919* (2013.01); *B29K 2071/00* (2013.01); *B29C 69/02* (2013.01); *B29L 2023/007* (2013.01); *A61N 1/0568* (2013.01); *B29C 65/02* (2013.01); *B29C 66/71* (2013.01); *B29C 66/1222* (2013.01); *B29K 2083/00* (2013.01); *A61N 1/05* (2013.01); *B29C 66/53241* (2013.01); *B29L 2031/753* (2013.01); *B29C 66/1224* (2013.01)
USPC .......................................................... 264/250

(58) Field of Classification Search
CPC ............ B29C 45/14549; B29C 66/919; B29C 66/91945; B29C 65/02; B29C 66/1222; B29C 66/53241; B29C 66/71
USPC .......................................................... 264/250
See application file for complete search history.

(56) References Cited

U.S. PATENT DOCUMENTS

| | | | | |
|---|---|---|---|---|
| 4,405,553 | A  * | 9/1983 | Lovgren et al. | 264/272.19 |
| 6,361,780 | B1 * | 3/2002 | Ley et al. | 424/400 |

(Continued)

FOREIGN PATENT DOCUMENTS

WO    WO2011081699 A1    7/2011

OTHER PUBLICATIONS

International Search Report and Written Opinion issued in PCT/US2013/024884, mailed May 7, 2013, 13 pages.

*Primary Examiner* — Amjad Abraham
(74) *Attorney, Agent, or Firm* — Faegre Baker Daniels LLP (57) ABSTRACT

Methods of manufacturing implantable medical devices with one or more undermolded features are disclosed. An example method includes injection molding an annular-shaped member onto an inner surface of a sacrificial mold insert, and then undermolding an elongate medical device body directly to the member. The member is directly coupled to the device body without the use of adhesives or bonding agents, thus eliminating the presence of gaps or surface irregularities that can affect device performance.

20 Claims, 7 Drawing Sheets

(56) References Cited

U.S. PATENT DOCUMENTS

| | | | |
|---|---|---|---|
| 2008/0027526 A1* | 1/2008 | Zarembo | 607/120 |
| 2010/0049288 A1* | 2/2010 | Westlund et al. | 607/122 |
| 2010/0115770 A1* | 5/2010 | Eggert et al. | 29/877 |
| 2010/0125320 A1 | 5/2010 | Polkinghorne et al. | |
| 2010/0145423 A1* | 6/2010 | Seifert | 607/116 |
| 2010/0210146 A1 | 8/2010 | Jang et al. | |
| 2011/0160831 A1 | 6/2011 | De Kock et al. | |
| 2012/0020791 A1* | 1/2012 | Flemming et al. | 416/146 R |

\* cited by examiner

STEROID ELUTING COLLAR UNDERMOLD

CROSS-REFERENCE TO RELATED APPLICATION

This application claims priority to Provisional Application No. 61/617,966, filed Mar. 30, 2012, which is herein incorporated by reference in its entirety.

TECHNICAL FIELD

The present disclosure relates generally to methods of manufacturing implantable medical devices. More specifically, the present disclosure pertains to methods of manufacturing implantable medical devices with undermolded features such as steroid-eluting drug collars, visual aids, and/or radioscopic traceable members.

BACKGROUND

Various types of medical electrical leads for use in cardiac rhythm management (CRM) and neurostimulation applications are known. In CRM applications, for example, such leads are frequently delivered intravascularly to an implantation location on or within a patient's heart, typically under the aid of fluoroscopy. Once implanted, the lead is coupled to a pulse generator or other implantable device for sensing cardiac electrical activity, delivering therapeutic stimuli, and/or for performing other desired functions within the body. Such leads typically include a distal conductor end with one or more electrodes that contact the heart tissue, and a proximal terminal end that is connected to a pacemaker or defibrillator. The conductor end of the lead can include one or more features such as an active fixation helix or a number of passive tines to facilitate securing the lead to the heart tissue. The terminal end of the lead, in turn, includes one or more electrical contacts that are electrically connected to the electrodes via a number of lead conductors.

An increase in the stimulation threshold required to electrically stimulate the body can result from the interaction of the electrodes with the body tissue at the site of implantation. In CRM applications involving leads implanted in or near the heart, for example, the capture threshold of the lead can increase due to the formation of scar tissue at the location where the electrodes contact the body tissue. Approaches to reducing the capture threshold have included the incorporation of drug-eluting collars or plugs containing a therapeutic drug such as dexamethasone acetate, which reduces inflammation at the site of contact.

The incorporation of drug-eluting collars or plugs into medical electrical leads is typically accomplished via an injection molding process in which the collar or plug is preformed as a separate component, and then subsequently bonded to the lead body via an adhesive or glue. In the fabrication of medical electrical leads used in CRM and neurostimulation applications, for example, the drug-eluting collar is typically formed in a mold and then adhesively bonded onto a distal portion of the lead, typically adjacent to an electrode located at the distal end of the lead body. In some cases, variability in the contact surface area at the location of the adhesive can cause the rate at which the drug is eluted into the body tissue to vary. Some drug collar bonding techniques can also result in yield fallout and other manufacturing issues.

SUMMARY

The present disclosure relates to methods of manufacturing implantable medical devices with undermolded features such as steroid-eluting drug collars, visual aids, and/or radioscopic traceable members.

In Example 1, a method of manufacturing an implantable medical device comprises: inserting a mold insert into a molding tool and molding a member onto an interior surface within an interior cavity of the mold insert; inserting an elongate medical device body into an interior lumen of the member; undermolding the elongate medical device body directly to the member; and removing the mold insert from the member.

In Example 2, the method according to Example 1, wherein molding a member onto an interior surface of the mold insert comprises: inserting an elongate rod into the interior cavity of the mold insert; and injection molding an annular-shaped ring onto the interior surface of the mold insert.

In Example 3, the method according to either Example 1 or 2, wherein the mold insert comprises a sacrificial disk.

In Example 4, the method according to Example 3, wherein the sacrificial disk comprises a polymeric or metallic material.

In Example 5, the method according to any of Examples 1-4, wherein undermolding the elongate medical device body directly to the member comprises molding the body onto an interior surface of the member.

In Example 6, the method according to any of Examples 1-5, wherein undermolding the elongate medical device body directly to the member comprises molding the device body onto an interior surface of the member.

In Example 7, the method according to any of Examples 1-6, wherein removing the mold insert from the member comprises cutting the mold insert away from the member.

In Example 8, the method according to any of Examples 1-7, wherein the medical device is an implantable medical electrical lead, and wherein the elongate medical device body is a lead body.

In Example 9, the method according to any of Examples 1-8, wherein the member comprises a drug-eluting collar.

In Example 10, a method of manufacturing an implantable medical electrical lead comprises: inserting a mold insert into a molding tool and molding a collar onto an interior surface within an interior cavity of the mold insert; inserting an elongate lead body into an interior lumen of the collar; undermolding the lead body directly to the collar; and removing the mold insert from the collar.

In Example 11, the method according to Example 10, wherein molding a collar onto an interior surface of the mold insert comprises: inserting an elongate rod into the interior cavity of the mold insert; and injection molding an annular-shaped collar onto the interior surface of the mold insert.

In Example 12, the method according to either Example 10 or 11, wherein the mold insert comprises a sacrificial disk.

In Example 13, the method according to Example 12, wherein the sacrificial disk comprises a polymeric or metallic material.

In Example 14, the method according to any of Examples 10-13, wherein undermolding the lead body directly to the collar comprises injection molding the lead body onto an interior surface of the collar.

In Example 15, the method according to any of Examples 10-14, wherein undermolding the lead body directly to the collar comprises molding the lead body onto an interior surface of the collar.

In Example 16, the method according to any of Examples 10-15, wherein removing the mold insert from the collar comprises cutting the mold insert away from the collar.

In Example 17, a medical electrical lead comprises: a lead body having a proximal section, a distal section, and an outer periphery; and at least one annular-shaped collar undermolded directly to the outer periphery of the lead body.

In Example 18, the medical electrical lead according to Example 17, wherein the collar is directly coupled to the outer periphery of the lead body via an adhesiveless bond.

In Example 19, the medical electrical lead according to Example 17, wherein the lead body is molded onto an interior surface of the collar.

In Example 20, the medical electrical lead according to any of Examples 17-19, wherein the at least one annular-shaped collar comprises a plurality of collars undermolded to the outer periphery of the lead body.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
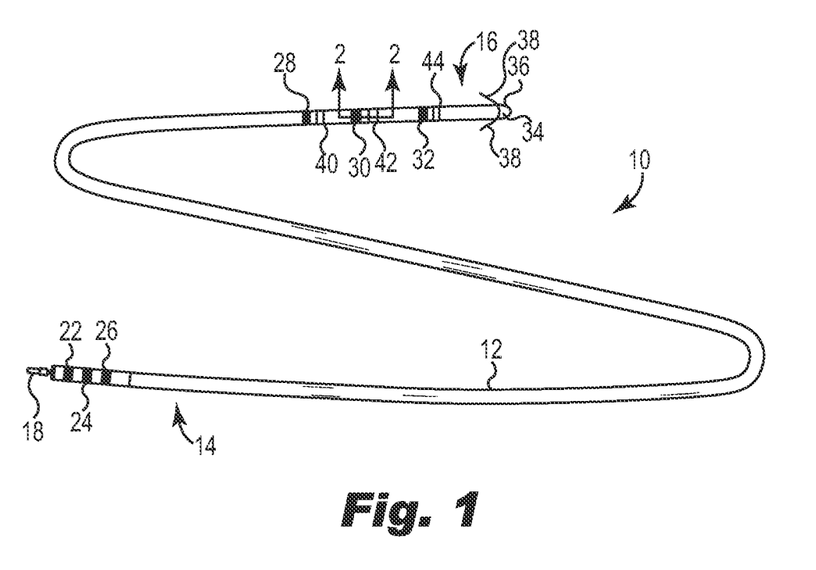
FIG. 1 is a perspective view showing an implantable medical device including an undermolded member in accordance with an illustrative embodiment.

FIG. 1 is a perspective view showing an implantable medical device 10 including an undermolded member. The device 10, illustratively an implantable cardiac lead configured for providing electrical stimulus therapy to and/or for sensing electrical activity within a patient's heart, comprises a lead body 12 having a proximal section 14 and a distal section 16. The proximal section 14 of the lead 10 includes a terminal pin 18 and a number of terminal ring contacts 22, 24, 26 that connect to a pacemaker, implantable cardioverter defibrillator (ICD), cardiac resynchronization therapy (CRT) device, or other pulse generator. The distal section 16 of the lead 10 includes a number of electrodes 28, 30, 32, 34 each coupled to a corresponding lead conductor within the interior of the lead body 12. In the embodiment of FIG. 1, for example, the lead 10 includes three ring electrodes 28, 30, 32 each electrically connected to a corresponding terminal contact 22, 24, 26 on the lead 10. A distal tip electrode 34 on the implantable lead 10 is electrically coupled to the terminal pin 18, and is located at or near the distal end 36 of the lead 10. A number of fixation tines 38 can be used to secure the distal end 36 of the lead 10 to cardiac tissue during the implantation process.

During operation, the pulse generator supplies electrical pulses to the electrodes 28, 30, 32, 34 for pacing the heart and/or for sensing cardiac electrical activity. A number of members 40, 42, 44 coupled to the lead body 12 are configured to delivery therapy to the body tissue, to serve as a visual aid or radioscopically traceable member for visualizing and/or locating the lead 10 within the body, and/or for performing other desired functions within the body. In some embodiments, for example, the members 40, 42, 44 each comprise a drug-eluting collar that delivers a therapeutic drug (e.g., dexamethasone acetate) into the body tissue adjacent to the ring electrodes 28, 30, 32. In the embodiment of FIG. 1, for example, each member 40, 42, 44 is disposed on the lead body 12 adjacent to an associated electrode 28, 30, 32, and is configured to deliver a drug to the body over a period of time in order to reduce inflammation at the site of contact between the electrodes 28, 30, 32 and the surrounding tissue. The members 40, 42, 44 can be configured to deliver other drugs and/or provide other types of therapy in addition to, or in lieu of, steroids used for the purpose of reducing insertion site inflammation. Other types of members can include, for example, ablation electrodes for providing ablation therapy to the body and radiopaque markers for fluoroscopically imaging the lead within the body.

Figure 2:
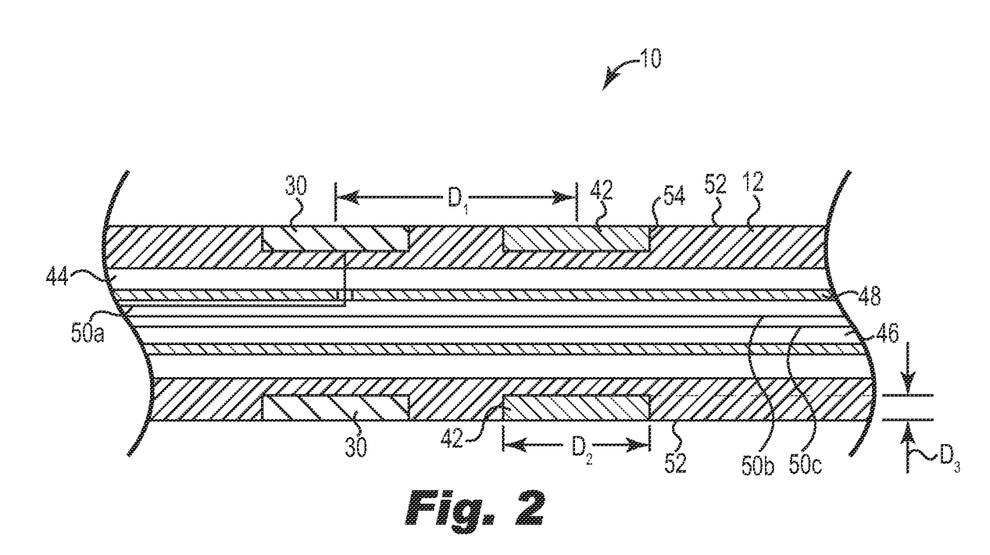
FIG. 2 is a cross-sectional view of the lead along line 2-2 in FIG. 1 showing one of the members coupled to the lead body.

FIG. 2 is a cross-sectional view of the lead 10 along line 2-2 in FIG. 1 showing one of the members 42 coupled to the lead body 12. As can be further seen in FIG. 2, the lead body 12 comprises an elongate, tubular shaped body including one or more interior lumens 44, 46 for housing several lead conductors 50a, 50b, 50c used for supplying electrical currents to the ring electrodes 28, 30, 32 and the distal tip electrode 34. The lead body 12 may also contain other lead components such as steering wires, fluid lumens, and/or a drive mechanism for engaging a fixation helix.

Each member 42 comprises an annular-shaped collar disposed about an outer periphery 52 of the lead body 12. The member 42 is spaced longitudinally apart from the ring electrode 30 via a longitudinal distance $D_1$. In some embodiments, the distance $D_1$ may be selected so as to permit drugs to be delivered to the contact site where the ring electrode 30 contacts the surrounding tissue. In some embodiments, for example, the member 42 is spaced longitudinally apart from the ring electrode 30 by a distance $D_1$ of between about 0.1 millimeters to about 10 millimeters, and more specifically, about 0.5 millimeters to about 0.7 millimeters. The length $D_2$ of the member 42 can vary from about 0.5 millimeters to about 10 millimeters, and more specifically, about 0.8 millimeters to about 2.5 millimeters. The thickness $D_3$ of the member 42, in turn, can vary from about 0.1 millimeters to about 1.0 millimeters, and more specifically, about 0.2 millimeters to about 0.3 millimeters. Other lengths $D_1$, $D_2$ and a thickness $D_3$ greater or lesser than these ranges are also possible depending on the configuration of the lead 10.

The member 42 is coupled directly to the lead body 12 via an undermolding process such that no gaps or spaces exist at the interface 54 between the member 42 and the lead body 12. The other members 40, 44 can also have a similar configuration so as to eliminate the presence of gaps or surface irregularities at other locations along the length of the lead body 12. As used herein, the term "directly coupled" indicates that the member 42 is in contact with the lead body 12 without any interstitial layers or members disposed in between the two components 12, 42. In some embodiments, for example, the interface 54 between the member 42 and the lead body 12 does not contain an adhesive or bonding agent, as is typically used in securing many conventional drug collars to the lead. As a result, the interface 54 is substantially devoid of any gaps or surface irregularities that can result from adhesive bonding. Several example steps that can be used for manufacturing an implantable medical device such as the lead 10 of FIGS. 1-2 are further described herein with respect to FIGS. 3 and 5A-5D.

In some embodiments, the material used in fabricating the lead body 12 and/or members 40, 42, 44 can be selected to facilitate thermal bonding of the members 40, 42, 44 directly onto the lead body 12 during an undermolding process. In some embodiments, for example, the members 40, 42, 44 are each formed from a base polymeric material that, when sufficiently heated onto the outer periphery 52 of the lead body 12 at a temperature below the melting point of the material, causes the lead body material to thermally bond with the member 40, 42, 44 material at the interface 54. An example polymeric material that can be used for this purpose is silicone, which can be thermally bonded to lead body materials such as silicone or polyether ether ketone (PEEK).

Figure 3:
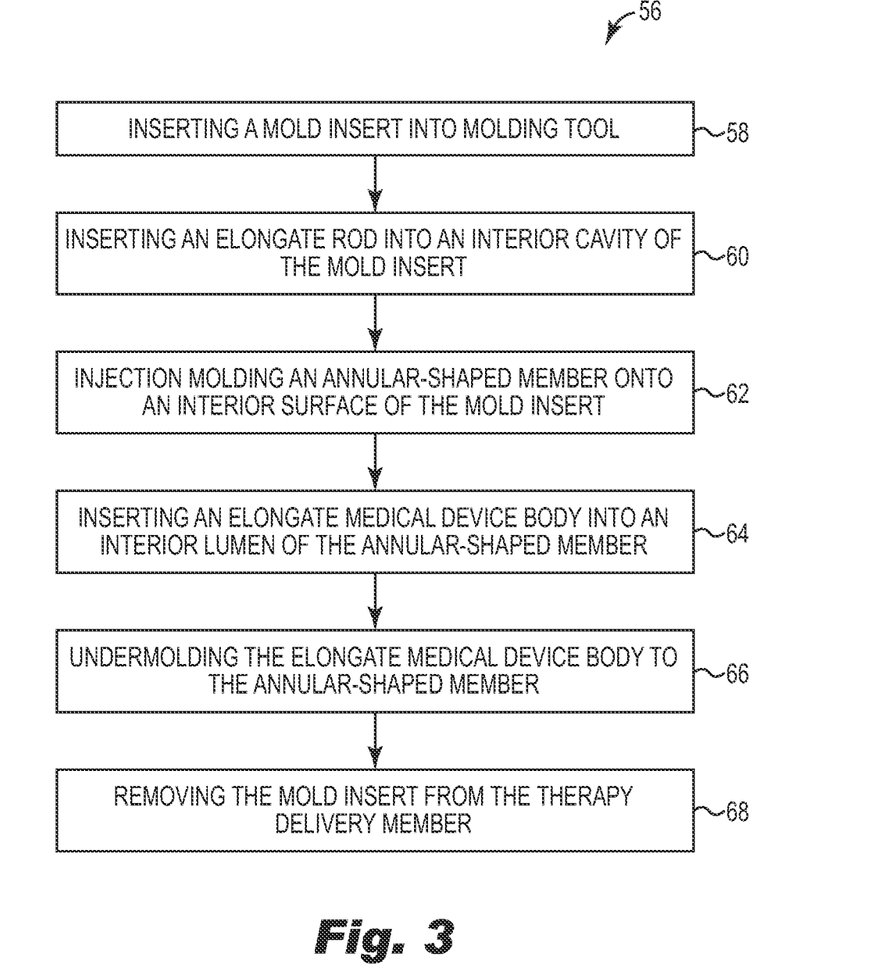
FIG. 3 is a flow diagram showing an example method of manufacturing an implantable medical device in accordance with an illustrative embodiment.

FIG. 3 is a flow diagram showing an example method 56 of manufacturing an implantable medical device. FIG. 3 may represent, for example, several example manufacturing steps that can be used for molding one or more drug-eluting collars onto a medical electrical lead such as the lead 10 of FIG. 1.

The method 56 may begin generally at block 58 in which a sacrificial mold insert is inserted into a molding tool such as a multi-cavity injection mold. In certain embodiments, for example, the sacrificial mold insert comprises a disk-shaped member that is used for initially forming an annular-shaped member independent of the lead body. During later steps, the mold insert also serves to facilitate undermolding of the lead body directly to an interior lumen of the member. An example sacrificial mold insert that can be used for this purpose is further described herein with respect to FIG. 4.

Once the mold insert is placed within the molding tool, an elongate member such as an elongate rod (e.g., a core pin) is then inserted into an interior cavity of the mold insert (block 60). The outer extent of the rod is suitably sized so that an annular-shaped space is formed within the molding tool in between the outer periphery of the elongate member and an interior surface formed by an interior cavity of the mold insert. With the elongate member disposed within the mold insert, a plastic resin containing the steroid is then injection molded into the space formed by the interior cavity of the mold insert (block 62). The mold insert along with the annular-shaped member are then removed from the molding tool.

Upon injection molding the member to the inner surface of the mold insert, an elongate medical device body is then inserted into an interior lumen of the annular-shaped member while the member is still attached to the mold insert (block 64). The medical device body and mold insert are then subjected to an undermolding process in order to undermold the medical device body directly to the annular-shaped member (block 66). During this process, the second molding tool is maintained at a suitable temperature to cause the material of the annular-shaped member to thermally bond to the material forming the medical device body without causing the two components to melt, thus forming an interface layer between the two components that is devoid of any gaps or surface irregularities.

Once the medical device body is undermolded to the annular-shaped member, the mold insert is then removed from about the member (block 68). In certain embodiments, for example, removal of the member from the mold insert can be accomplished by cutting the mold insert and then peeling the insert away from the member. In other embodiments, a press can be used to force the member out from within the interior cavity of the mold insert.

Additional processing steps can then be performed to fabricate the remaining portion of the device, as is well known in the art. If desired, one or more additional members (e.g., drug collars) can also be coupled to other locations along the medical device body by repeating the process of injection molding an annular-shaped member within an interior cavity of a mold insert, and then undermolding the medical device body directly to the member.

Figure 4:
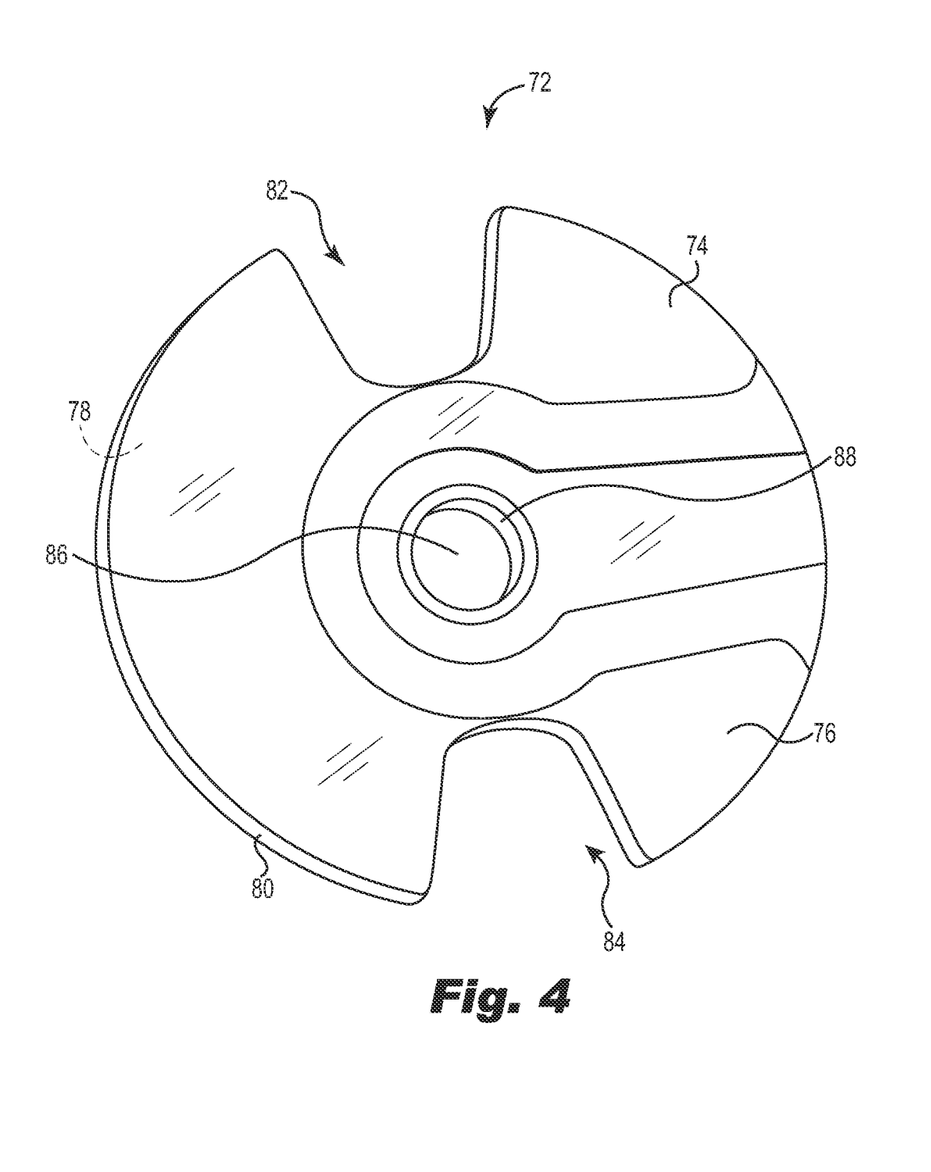
FIG. 4 is a perspective view showing a sacrificial mold insert that can be used in conjunction with the manufacturing method of FIG. 3.

FIG. 4 is a perspective view showing a sacrificial mold insert 72 that can be used in conjunction with the method 56 of FIG. 3. As shown in FIG. 4, the mold insert 72 comprises a disk-shaped insert body 74 having a first side 76, a second side 78, and a peripheral edge 80. A number of notches 82, 84 projecting inwardly from the peripheral edge 80 are used for aligning the mold insert within the molding tool, and to facilitate later removal of the mold insert 72 from the member during later processing steps.

An interior cavity 86 extending through the mold insert 72 from the first side 76 to the second side 78 defines an inner surface 88 that is sized to form the outer periphery of the member, once molded therein. The inner diameter of the interior cavity 86 will typically vary depending on the size of the medical device body. In medical electrical leads for use in cardiac and neurostimulation applications, for example, the inner diameter of the interior cavity 86 may vary in size from between about 1.0 millimeters to about 3.0 millimeters. Other sizes greater or smaller than these values are also contemplated. Although the mold insert 72 shown in FIG. 4 comprises a circular-shaped interior cavity 86, other shaped cavities are also possible in other embodiments. For example, in some embodiments the interior cavity 86 can have an oval, rectangular, or other non-symmetric cross-sectional shape.

The thickness of the mold insert 72 between the first and second sides 76, 78 defines the length of the member (as indicated by dimension $D_2$ in FIG. 2). For medical electrical leads, a suitable thickness of the mold insert 72 is between about 0.5 millimeters to about 10 millimeters, and more specifically, about 0.8 millimeters to about 2.5 millimeters. The thickness of the mold insert 72 can vary, however, depending on the specific length $D_2$ of the member to be fabricated.

In some embodiments, the mold insert 72 comprises a polymeric material having a melting point that is greater than that of the materials forming the lead body 12 and member 42. In one embodiment, for example, the mold insert comprises PEEK. In other embodiments, the mold insert is formed from a metal or a metal-polymer composite having a melting point greater than that of the materials forming the lead body 12 and member 42.

FIGS. 5A-5D are several views showing an example implementation of the method 56 of FIG. 3 for use in manufacturing a medical electrical lead 10 with one or more members.

Figure 5A:
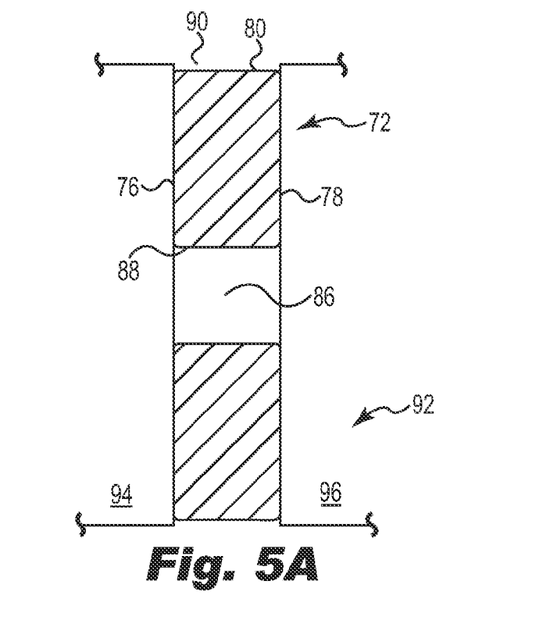
FIGS. 5A-5D are several views showing an example implantation of the method of FIG. 3 for use in manufacturing a medical electrical lead with one or more members.

In a first view shown in FIG. 5A, the sacrificial mold insert 72 is first inserted into the cavity 90 of a multi-cavity molding tool 92. In some embodiments, the molding tool 92 comprises a number of mold plates 94, 96 and one or more nozzles (not shown) for injecting plastic resin into the interior cavity 86 of the mold insert 72 once the insert 72 is placed into the mold cavity 90.

Figure 5B:
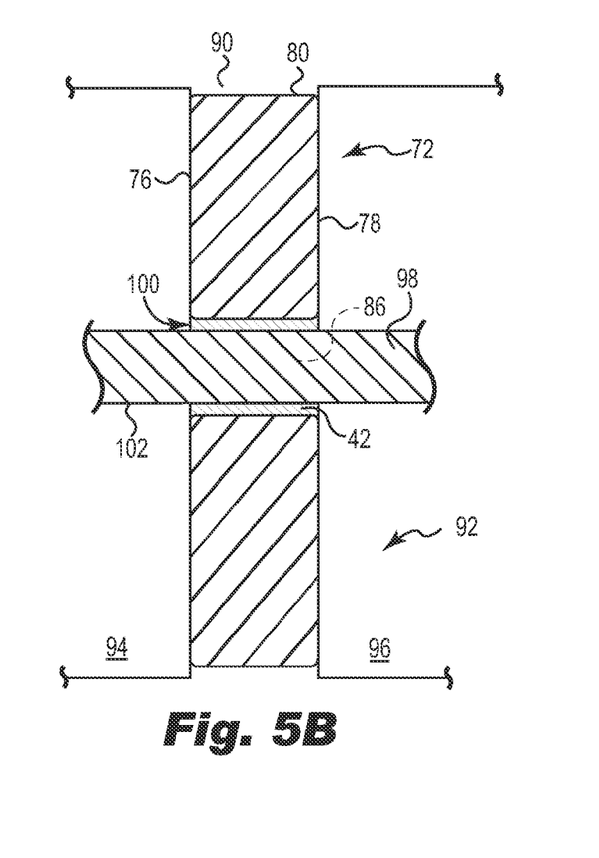

FIG. 5B is a view showing the insertion of an elongate member 98 (e.g., an elongate rod) into the interior cavity 86 of the mold insert 72. With the elongate member 98 inserted into the interior cavity 86, and as further shown in FIG. 5C, plastic resin is then injected into the mold 92 and into the space 100 located between the inner surface 88 of the mold insert 72 and the outer periphery 102 of the elongate member 98. This annular-shaped space 100, when injected with the plastic resin, corresponds in size and shape to the final member later assembled to the lead body.

Figure 5C:
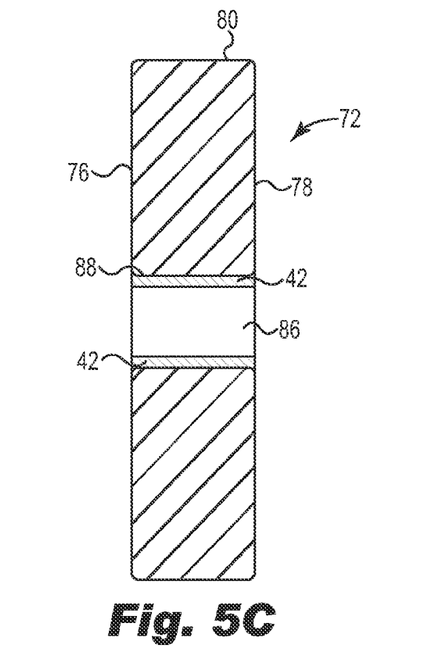

FIG. 5C is a view showing the formation of an annular-shaped member (e.g., member 42 of FIG. 2) after the elongate member 98 has been removed from within the mold insert 72, and once the mold insert 72 and accompanying member 42 have been removed from the molding tool 92.

Figure 5D:
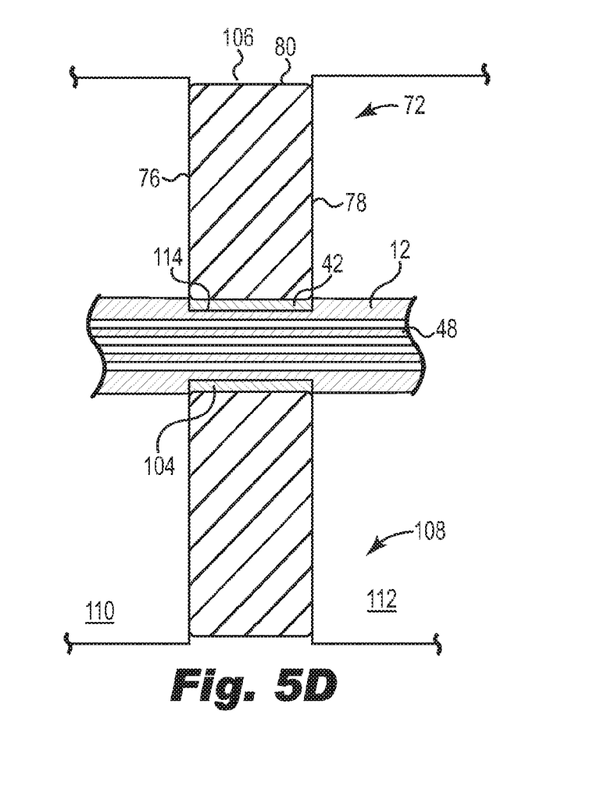

FIG. 5D is a view showing the mold insert 72 and member 42 inserted into the interior cavity 106 of another molding tool 108 including a number of mold plates 110, 112. As can be seen in FIG. 5D, the lead body 12 is inserted into the interior lumen of the member 42, and the mold plates 110, 112 are brought together while applying heat, causing the lead body 12 to undermold to the inner surface 114 of the member 42. During this step, the lead body 12 and member 42 are both maintained at a temperature sufficient to cause the member 42 to thermally bond to the lead body 12, but without melting. In certain embodiments, for example, the molding tool 108 is maintained at a temperature of about 130° C. for a period of about 60 seconds to about 300 seconds when a polymeric material such as silicone is used in forming the lead body 12 and member 42. The temperature and duration will typically vary depending on the material or materials used in forming the lead body 12 and/or the member 42.

Figure 6:
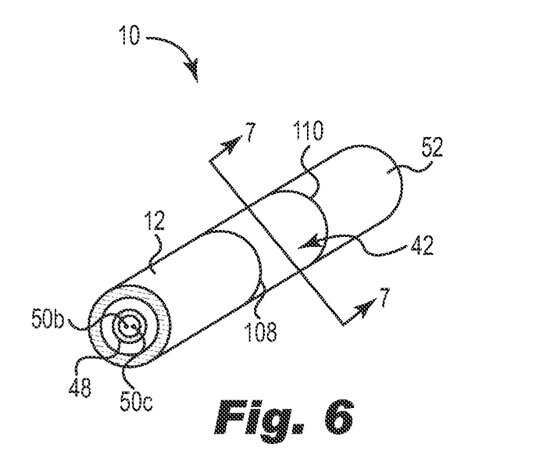
FIG. 6 is a perspective view showing a portion of the lead body once undermolded to the member in FIG. 5D.
Figure 7:
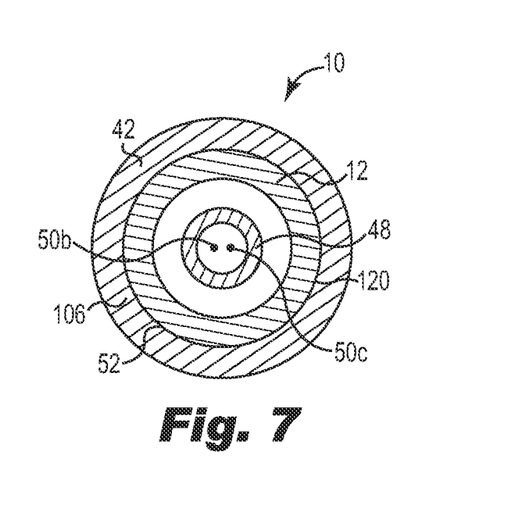
FIG. 7 is a cross-sectional view showing the lead body and member across line 7-7 in FIG. 6.

FIG. 6 is a perspective view showing a portion of the lead body 12 once undermolded to the member 42 in FIG. 5D. FIG. 7, in turn, is a cross-sectional view showing the lead body 12 and member 42 across line 7-7 in FIG. 6. As can be seen in FIG. 7, the member 42 is directly coupled about a circumferential interface 120 to the outer periphery 52 of the lead body 12 without the use of any adhesives or bonding agents. As a result, the outer surface 52 of the lead body 12 at the location of the member 42 is substantially devoid of any gaps or surface irregularities that can affect the desired performance characteristics of the lead 10.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A method of manufacturing an implantable medical device, comprising:
    inserting a mold insert into a molding tool and molding a member onto an interior surface within an interior cavity of the mold insert, the mold insert comprising a disk having a first side, a second side opposite the first side, and a peripheral edge, the molding tool comprising plates that engage the first and second sides of the disk to secure the mold insert during the molding;
    inserting an elongate medical device body into an interior lumen of the member while the member remains molded onto the interior surface of the mold insert;
    undermolding the elongate medical device body directly to the member to cause material defining the interior lumen of the member to thermally bond to material of the elongate medical device body while the member remains within the interior cavity the mold insert; and
    removing the mold insert from the member after the undermolding step.

2. The method of claim 1, wherein molding a member onto an interior surface of the mold insert comprises:
    inserting an elongate rod into the interior cavity of the mold insert; and
    injection molding an annular-shaped ring onto the interior surface of the mold insert.

3. The method of claim 1, wherein the disk comprises a sacrificial disk.

4. The method of claim 1, wherein the at least one plate comprises a pair of plates that respectively engage the first side and the second side of the disk to secure the mold insert during the molding.

5. The method of claim 1, wherein undermolding the elongate medical device body directly to the member comprises molding the body onto an interior surface of the member.

6. The method of claim 1, wherein the disk comprises at least one notch projecting inwardly from the peripheral edge, the at least one notch aligning the mold insert within the molding tool.

7. The method of claim 1, wherein removing the mold insert from the member comprises cutting the mold insert away from the member.

8. The method of claim 1, wherein the medical device is an implantable medical electrical lead, and wherein the elongate medical device body is a lead body.

9. The method of claim 1, wherein the member comprises a drug-eluting collar.

10. A method of manufacturing an implantable medical electrical lead, comprising:
    inserting a mold insert into a molding tool and molding a collar onto an interior surface within an interior cavity of the mold insert, wherein the mold insert comprises a disk and the molding tool engages opposite sides of the disk to secure the disk within the molding tool during the molding;
    inserting an elongate lead body into an interior lumen of the collar while the collar remains molded onto the interior surface of the mold insert;
    undermolding the lead body directly to the collar to cause material defining the interior lumen of the collar to thermally bond to material defining an exterior of the lead body while the collar remains within the interior cavity the mold insert; and
    removing the mold insert from the collar after the undermolding step.

11. The method of claim 10, wherein molding a collar onto an interior surface of the mold insert comprises:
    inserting an elongate rod into the interior cavity of the mold insert; and
    injection molding an annular-shaped collar onto the interior surface of the mold insert.

12. The method of claim 10, wherein the mold insert comprises a sacrificial disk.

13. The method of claim 12, wherein the molding tool comprises a pair of plates that respectively engage opposite sides of the disk to secure the mold insert during the molding.

14. The method of claim 10, wherein undermolding the lead body directly to the collar comprises injection molding the lead body onto an interior diameter surface of the collar.

15. The method of claim 10, wherein undermolding the lead body directly to the collar comprises molding the lead body onto an interior surface of the collar.

16. The method of claim 10, wherein removing the mold insert from the collar comprises cutting the mold insert away from the collar.

17. A method of manufacturing an implantable medical electrical lead, comprising:
- inserting a mold insert into a molding tool, the molding tool comprising a pair of plates;
- bringing the pair of plates together to clamp the mold insert in the molding tool;
- inserting an elongate rod into an interior cavity of the mold insert;
- injection molding a polymeric collar, the collar molded such that an exterior surface of the elongate rod forms an interior lumen of the collar and an interior surface of the interior cavity of the mold insert forms an exterior surface of the collar;
- removing the elongate rod while the collar remains within the interior cavity of the mold insert;
- inserting an elongate polymeric lead body into the interior lumen of the collar while the collar remains within the interior cavity of the mold insert;
- undermolding the lead body directly to the collar to cause polymeric material defining the interior lumen of the collar to thermally bond to polymeric material of the lead body while the collar remains within the interior cavity the mold insert; and
- removing the collar from within the interior cavity of the mold insert after the undermolding step.

18. The method of claim 17, wherein the mold insert is metallic.

19. The method of claim 17, wherein the mold insert is formed from a polymeric material having a higher melting temperature than the polymeric material that defines the collar.

20. The method of claim 17, wherein the mold insert is a disk.

* * * * *